(12) United States Patent
Deplancke et al.

(10) Patent No.: US 11,872,559 B2
(45) Date of Patent: Jan. 16, 2024

(54) DEVICE FOR HIGH THROUGHPUT SINGLE-CELL STUDIES

(71) Applicant: ECOLE POLYTECHNIQUE FEDERALE DE LAUSANNE (EPFL), Lausanne (CH)

(72) Inventors: Bart Deplancke, Cugy (CH); Johannes Bues, Lausanne (CH); Riccardo Dainese, Bussigny-Lausanne (CH); Marjan Biocanin, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 735 days.

(21) Appl. No.: 16/333,297

(22) PCT Filed: Sep. 13, 2017

(86) PCT No.: PCT/IB2017/055524
§ 371 (c)(1),
(2) Date: Mar. 14, 2019

(87) PCT Pub. No.: WO2018/051242
PCT Pub. Date: Mar. 22, 2018

(65) Prior Publication Data
US 2019/0240664 A1 Aug. 8, 2019

(30) Foreign Application Priority Data
Sep. 14, 2016 (EP) .................................. 16188796

(51) Int. Cl.
*B01L 3/00* (2006.01)
*C12Q 1/6806* (2018.01)
(Continued)

(52) U.S. Cl.
CPC ... *B01L 3/502753* (2013.01); *B01L 3/502715* (2013.01); *B01L 3/502738* (2013.01);
(Continued)

(58) Field of Classification Search
CPC ......... B01L 3/502753; B01L 3/502715; B01L 3/502738; B01L 3/502784;
(Continued)

(56) References Cited

U.S. PATENT DOCUMENTS

2008/0014589 A1   1/2008   Link et al.
2015/0298091 A1  10/2015   Weitz et al.

FOREIGN PATENT DOCUMENTS

CN   105 907 840   8/2016

OTHER PUBLICATIONS

Ho, Kenneth, et al, Mechanically activated artificial cell by using microfluidics, Scientific Reports, Sep. 9, 2016, 6:32912. (Year: 2016).*

(Continued)

*Primary Examiner* — Christine T Mui
(74) *Attorney, Agent, or Firm* — Nixon & Vanderhye P.C.

(57) ABSTRACT

The present invention concerns a microfluidic device or chip including at least one inlet for introducing at least one object into the device; an oil inlet for introducing an oil that supports droplet formation into the device or a droplet forming substance inlet for introducing a droplet forming substance into the device; a co-encapsulation area or structure where the at least one object is encapsulated by the droplet; a microfluidic tubing or channel for transporting the at least one object to an entrance of the co-encapsulation area or structure; an oil supporting droplet formation microchannel or droplet forming substance microchannel connected to the microfluidic tubing or channel to place a liquid of the microfluidic tubing or channel in direct contact with (Continued)

Figure 1:
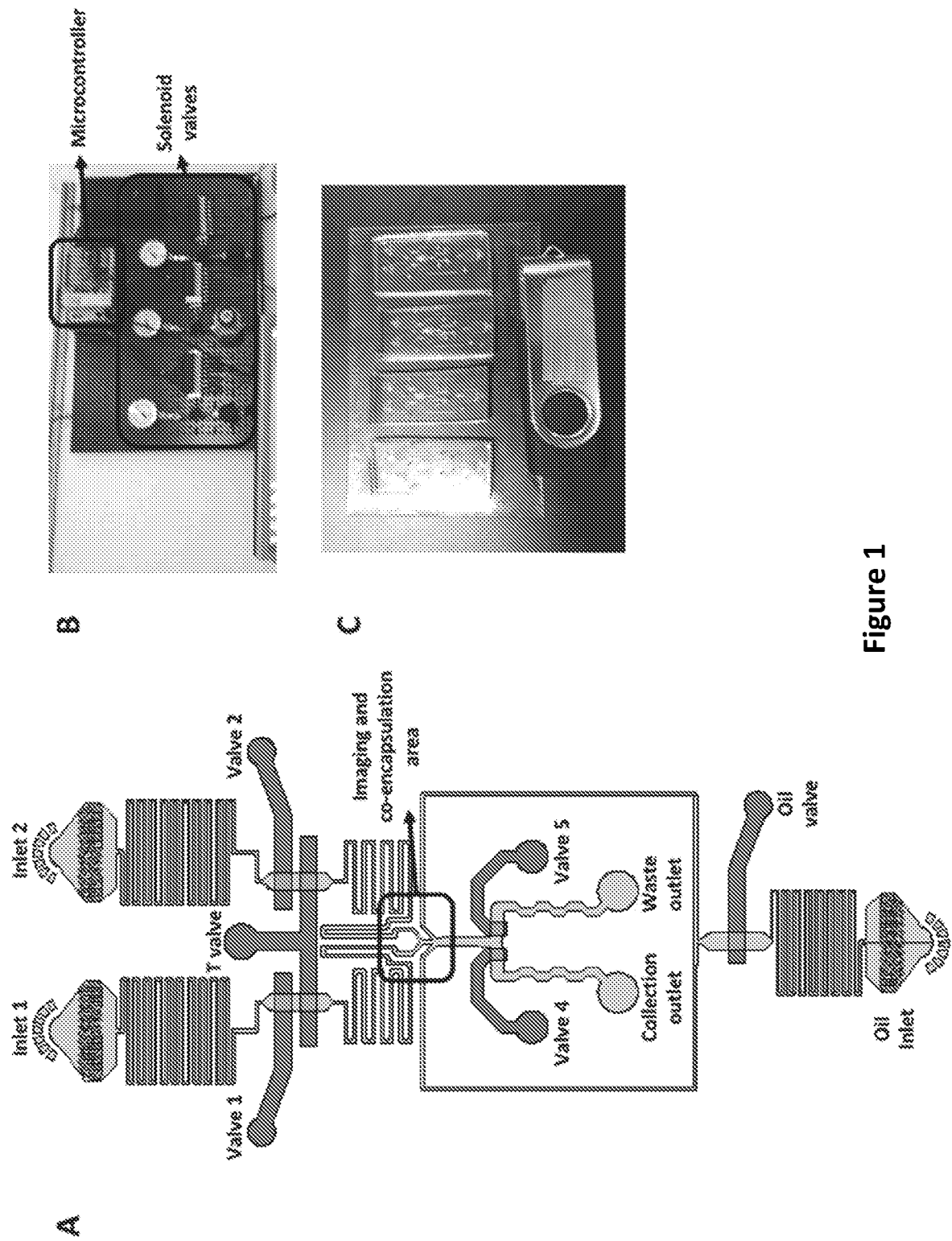

the oil that supports droplet formation or the droplet forming substance; and a droplet microchannel or tubing for transporting the droplet.

19 Claims, 17 Drawing Sheets

(51) Int. Cl.
*G06T 7/00* (2017.01)
*C12Q 1/00* (2006.01)

(52) U.S. Cl.
CPC ...... *B01L 3/502784* (2013.01); *C12Q 1/6806* (2013.01); *G06T 7/0014* (2013.01); *B01L 2300/0883* (2013.01); *B01L 2400/0481* (2013.01); *B01L 2400/0655* (2013.01)

(58) Field of Classification Search
CPC ..... B01L 2300/0883; B01L 2400/0481; B01L 2400/0655; G06T 7/0014; G06T 7/0012; G06T 7/0002; G06T 7/00; C12Q 1/6806
USPC .................................................. 422/502, 500
See application file for complete search history.

(56) References Cited

OTHER PUBLICATIONS

International Search Report for PCT/IB2017/055524 dated Nov. 29, 2017, 5 pages.
Written Opinion of the ISA for PCT/IB2017/055524 dated Nov. 29, 2017, 8 pages.
Lagus et al., "High-throughput co-encapsulation of self-ordered cell trains: cell pair interactions in microdroplets", RSC Advances, vol. 3, No. 43, Aug. 21, 2013, pp. 20512-20522.
Cao et al., "Droplet sorting based on the number of encapsulated particles using a solenoid valve", Lab on a Chip, vol. 13, No. 1, Oct. 19, 2012, 8 pages.
Collins et al., "The Poisson distribution and beyond: methods for microfluidic droplet production and single cell encapsulation", Lab on a Chip, vol. 15, No. 17, Jan. 1, 2015, pp. 3439-3459.
Zeng et al., "Microvalve-actuated precise control of individual droplets in microfluidic devices", Lab on a Chip, vol. 9, No. 10, Jan. 1, 2009, pp. 1340-1343.

* cited by examiner

| Valve | 1 | 2 | 3 | 4 | 5 | 6 |
|---|---|---|---|---|---|---|
| Valve description | particle 1 | particle 2 | T-valve | oil | waste | sample |
| detect particle | 0 | 0 | 0 | 1 | 0 | 1 |
| stop particle | 1 | 1 | 0 | 1 | 0 | 1 |
| flush oil | 1 | 1 | 0 | 0 | 0 | 1 |
| eject particle | 1 | 1 | 1 | 1 | 0 | 1 |
| form & capture droplet | 1 | 1 | 1 | 0 | 1 | 0 |

DEVICE FOR HIGH THROUGHPUT SINGLE-CELL STUDIES

CROSS-REFERENCE TO RELATED APPLICATIONS

This application is the U.S. national phase of International Application No. PCT/IB2017/055524 filed Sep. 13, 2017 which designated the U.S. and claims priority to the European patent application with the application No. EP16188796.3 filed on Sep. 14, 2016, the entire contents of each of which are hereby incorporated by reference

FIELD OF THE INVENTION

The present invention relates to a device or system for high throughput single-cell studies and more particularly to a soft microrobotic device or system for high throughput single-cell studies.

In particular, the present invention presents an innovative approach for real-time selection and manipulation of single cells and single microparticles on a microfluidic chip.

More specifically the present invention relates to: 1) the on-chip integration of multilayer microfluidics, droplet microfluidics, real-time image processing and machine learning. 2) the use for example of this integrated platform in order to monitor and manipulate with arbitrary accuracy the position of single microparticles (including single cells) in a microfluidic chip. 3) the use for example of this platform in order to deterministically co-encapsulate an arbitrary amount of single microparticles in an arbitrary amount of single water-in-oil droplets. 4) the use for example of the platform in order to study lowly abundant cell populations with single-cell accuracy and with infinitesimal sample loss.

Since the key element and goal of this technology is the DeterminIStic CO-encapsulation of microparticles, it is thus referred to as DISCO.

DISCO constitutes a grand opportunity of general applicability for both industries and academia. The main reasons for this are:

1) There is immense diversity in the chemical composition and biofunctionalization of commercially available, synthesizable and naturally occurring microparticles. On one hand, in order to dissect the diversity of naturally occurring microparticles (e.g. cells, microvescicles and microorganisms) the ability of studying them in isolation is required. On the other hand, the large number of commercially available microparticles with ad-hoc chemical and surface properties opens an equally large number of opportunities. For example, an innovative technology developed by Macosko and colleagues, called Drop-seq, exemplifies the potential of co-encapsulating ad-hoc functionalized beads with cells in order to extract and study a molecular species of interest from single cells in a high throughput fashion.
2) Droplet microfluidics offers the possibility of performing the mentioned co-encapsulation in microscopic water-in-oil microreactors. This allows for:
   a. minimal sample volume consumption which translates into affordability and portability.
   b. substantial freedom in the design of the experiments given that any water-based solution can be used.
   c. very high efficiency of chemical reactions occurring in the microreactor given its nanoliter/picoliter scale volume.
3) Multilayer microfluidics provides the exquisite on-chip control of flow-rate and particle positioning by using micromechanical valves. The integration with droplet microfluidic enables us to turn the process of particle co-encapsulation from stochastic (as in Macosko et al.) to deterministic. This translates in even smaller experimental volumes and infinitesimal sample losses. This property becomes crucial when only a limited number of cells/microparticles are being studied.
4) The integration of on-chip real-time image processing further increases the potential of the technology. For example, as opposed to other microfluidic-based single-cell technologies like the Fluidigm C1 and Drop-seq, where target cells enriched through FACS sorting before being loaded on-chip, our platform aims to perform optical cell/microparticle selection directly on chip, thus inducing minimal stress on the biological material and increasing the affordability of the platform.
5) Finally, another great platform novelty of general applicability is the integration of machine learning techniques for orchestrating and automating all the tasks mentioned above. A single digital processing unit can be used to collect images, analyze them in real-time, calculate microparticle properties (e.g. size, speed and position), control all micromechanical valves and adjust flow input pressures. The novelty mainly resides in conceiving DISCO as the first biocompatible, microfluidic soft-robot.

POTENTIAL INDUSTRIAL APPLICATIONS

1. Deterministic Cell/Bead Co-Encapsulation for High Throughput Single-Cell RNA-Seq.
   The first area of application of this invention is single-cell transcriptomics, which has the aim of dissecting the complex genome-wide determinants of single-cell heterogeneity. The most popular single-cell RNA-seq techniques are Fluidigim's C1 and Drop-seq. These technologies still required a substantial cell number input (>1000 cells of which many are lost) and cannot perform on-chip selection. This is a key advantage of our platform where an arbitrary number of cells can be processed with 100% efficiency and on-chip selection. These attributes are appealing both to academia and clinical research where sensitivity and efficiency of detection is crucial. In particular, we also speculate that on-chip selection induces a much smaller stress on cells and gives them much less time to transcriptionally react to that stress, as opposed to FACS sorting, thus yielding much cleaner and accurate transcriptional profiles.
2. Multicellular Co-Encapsulation for Cell-Cell Interaction Studies
   An equally straightforward application is the extension of the above mentioned protocol in order to co-encapsulate single cells with other single cells instead of beads.
   For example, as in Dura et al. where single-cell lymphocytes pairs are studied in terms of the response to the mutual interaction. Once again, in the mentioned study the pair formation was stochastic and many single lymphocytes were left without a partner. Instead, this invention would enable the controlled formation of an arbitrary number of pairs. Furthermore, for the first time, this invention would enable not only the controlled formation of pairs but the controlled formation of triplets, quadruplets etc., thus opening radically new possibilities for studying cell-cell interaction and multicellular aggregation.

3. Multiplexed Single-Cell Studies

As mentioned above, this invention can enable the co-encapsulation in one single compartmentalized water-in-oil droplet of an arbitrary number of microparticles. Therefore, single cells can be co-encapsulated not only with beads containing primers for mRNA capturing, but also with beads functionalized with other organic species like antibodies or aptamers. This would enable for the first high throughput and multiplexed extraction of different molecular species from single cells.

4. Detection and Analysis of Rare Cell Types in Human Liquids

Towards more clinical significance, a natural extension of the previous points is the ability to load on chip, select and analysis rare cell types directly from unpurified human samples. Importantly, a great possibility offered by this invention would be the detection of diseased state based on the multiplexed analysis of single cells (e.g. based on gene expression, chromatin state and protein data).

5. Isolation and Culturing of Rare or Medically Relevant Cell Types

Another radically new avenue opened by this invention will be the possibility of isolating rare or medically relevant cells directly from unpurified human samples and selectively culture them directly inside water-in-oil droplets.

6. High-Resolution Flow Imaging of Particle Suspension

As the invention allows for coordination of particles, and hence stopping them in a fixed position on defined regions on the chip, highly complex imaging approaches can be used to analyze particles. For example multi acquisition imaging approaches, like confocal imaging, focal stack acquisition, particle topology analysis by phase-imaging, super-resolution imaging, etc. which require a sample fixed in space, could be applied. This is impossible with current flow-imaging approaches, acquiring images of moving particles without stopping them. This application could be especially valuable for high resolution morphological studies on large number of cells in a defined setting.

7. Deterministic Pairing of Particles with Liquid Reagents

As the invention allows for coordination of particles before encapsulation, particles could be encapsulated with defined reagents from a multiplexer channel. As current methods don't allow for deterministic encapsulation of particles in droplets, they can't deterministically pair each particle with a different reagent. This application could be particularly interesting for personalized medicine, in which rare cells (e.g. circulating tumor cells) could be each paired with an individual drug (or drug combination) to determine efficient therapy approaches. Furthermore, this application could be useful for deterministic barcoding of cells, in which each cell is encapsulated with a solution containing individually barcoded reagents (e.g. oligonucleotide sequences).

ACCOMPLISHMENTS OF THE INVENTION

Designed, fabricated and optimized a multilayer microfluidic chip the supports high throughput water-in-oil droplets and implements a system of micromechanical valves for the control of flow and microparticle position.

Built a digital circuit for the computerized control of input flow pressure, micromechanical valves actuation and image collection.

Designed and implemented machine learning code in order to perform microrobotic tasks on chip.

Developed machine vision software to detect particles in microfluidics channels in real-time Developed particle coordination approach controlled by machine vision and computer actuated valves Developed droplet on-demand approach for steady fluids Developed autonomous deterministic co-encapsulation device

BACKGROUND OF THE INVENTION

One of the fundamental and most compelling challenges of the $21^{st}$ century is the molecular-level understanding of macroscale biological phenomena. The challenge stems from the immense complexity of biological networks. These networks are inherently multiscale and go from organism-level networks (e.g. ecosystems), to cellular-level networks (e.g. neural networks), to molecular-level networks (e.g. gene regulatory networks). Surprisingly, the decrease in network scale is not accompanied by a decrease in its complexity, rather the opposite is true.

If we are to dissect the complexity of these networks, we need to first exclude as much as possible sources of noise and heterogeneity among different networks; secondly, we need multiplexed tools that are able, provided a network, to simultaneously extract as much information as possible (i.e. as many molecular species as possible); thirdly we need to collect data for as many networks as possible in order to reconstruct their topology and properties with high confidence.

Therefore, the life sciences fields are in need of ever more powerful and sophisticated tools in order to dissect these networks. This invention, even though the underlying technology is of wider applicability, mainly pertains to the context of the study of gene regulatory networks. Shortly, gene regulatory networks (GRNs) are composed by proteins, DNA, RNA and their interactions. Several technologies have recently emerged which are able to probe specific molecular species in GRNs; one of the most developed techniques is RNA-seq, which is able to provide genome wide mRNA profiles of a given cell population.

In this context microfluidic proved to be able to push the experimental limitations, by making high throughput single cell RNA-seq a reality (e.g. in the case of Fluidigm C1 and Drop-seq). For the first time the mRNA content a high number of single cells (thus excluding population heterogeneity) can be analyzed in parallel with very low noise.

Nevertheless, these technologies still have limitations. For example, the inefficiency of the cell isolation process demands a large number of cells as a starting material, many of which are lost during the experiment. Also, if an heterogeneous cell population is used, the target cells have first to be enriched through FACS or MACS sorting, which can be stressful for the cells and can lead to changes in their mRNA profile, thus introducing experimental noise.

Furthermore, these target only mRNA and the other components or the GRN are lost.

Innovation compared to "WO 2016040476 A1 A droplet-based method and apparatus for composite single-cell nucleic acid analysis" (Drop-seq's patent):

Single-cell capture efficiency is radically improved (from 5-15% cell recovery rate to >80% or >90% in DISCO) as well as the complete elimination of the possibility of having cell doublets (i.e. two cells or two beads in the same droplet)

DISCO opens the possibility of selecting which cell types to encapsulate with beads.

DISCO is modular and can accommodate multiplexed experiments where not only mRNA but other cellular species can be extracted and analyzed.

Innovation compared to "U.S. Pat. Nos. 6,767,706, 7,040,338, 7,216,671, 7,479,186, 7,704,735, 7,766,055, 8,105,553, 8,105,824, 8,257,666, 8,273,574, 8,389,960, 8,455,258, 8,673,645, 8,871,446":

Single-cell capture efficiency is improved (from 5% cell recovery rate to >80% or >90% in DISCO) as well as the complete elimination of the possibility of having cell doublets (i.e. two cells or two beads in the same droplet)

DISCO can accommodate an arbitrarily high number of cells whereas Fludigm's trap based system only allows for the capture of a limited amount of cells DISCO is modular and can accommodate multiplexed experiments where not only mRNA but other cellular species can be extracted and analyzed.

FACS is needed before experiment, where DISCO can perform on-chip selection of cells of interest.

Innovation compared to "US 20150247790 A1 Microfluidic Assisted Cell Screening"

Particle stopping in the here shown particle coordination approach is machine vision based and completely independent of traps. Hence, the approach here is entirely size independent, is not prone to trap multiple particles as they are not stopped by trapping, and flow control can be exerted from a remote site of the channel.

Innovation compared to "U.S. Pat. No. 8,820,538 B1 Method and apparatus for particle sorting"

Particle coordination in the here described particle coordination approach allows for controlled particle movement, position, and downstream processing on chip, as compared to only detection and ejection in U.S. Pat. No. 8,820,538 B1.

This invention aims to address this limitation with a novel integrative approach.

SUMMARY

It is therefore one aspect of the present disclosure to provide a microfluidic device or chip according to claim 1. Further advantageous features can be found in the dependent claims.

A BRIEF DESCRIPTION OF THE DRAWINGS

Figure 2:
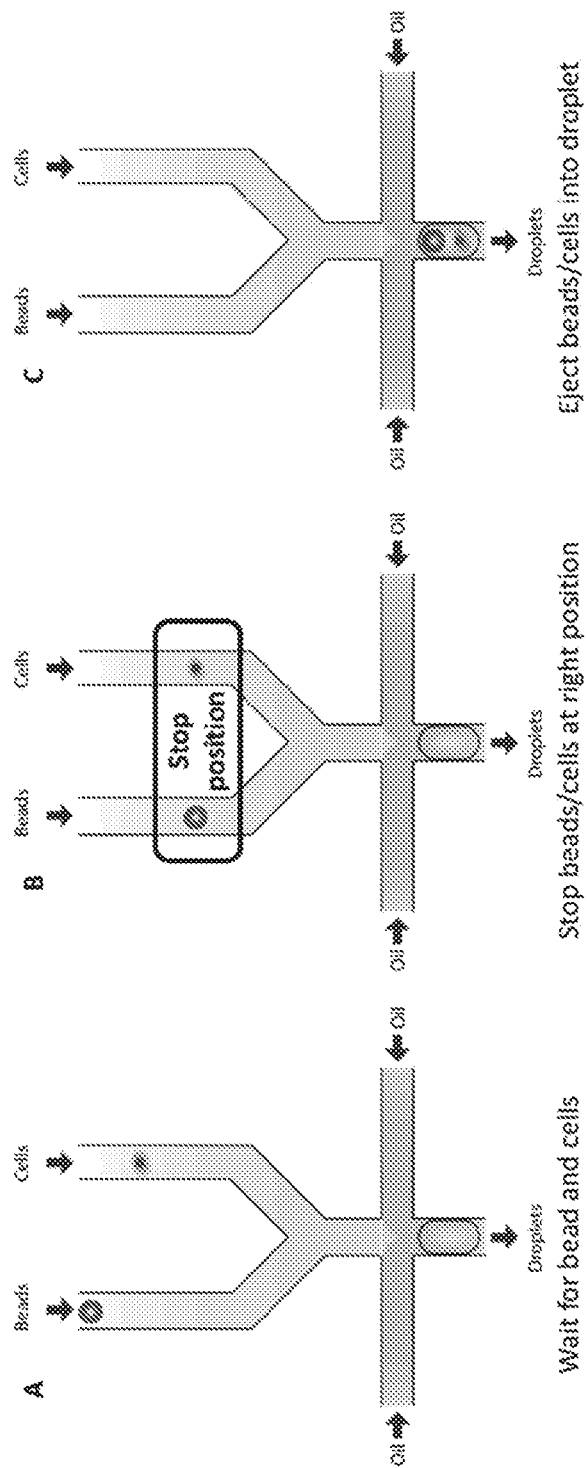
Figure 3:
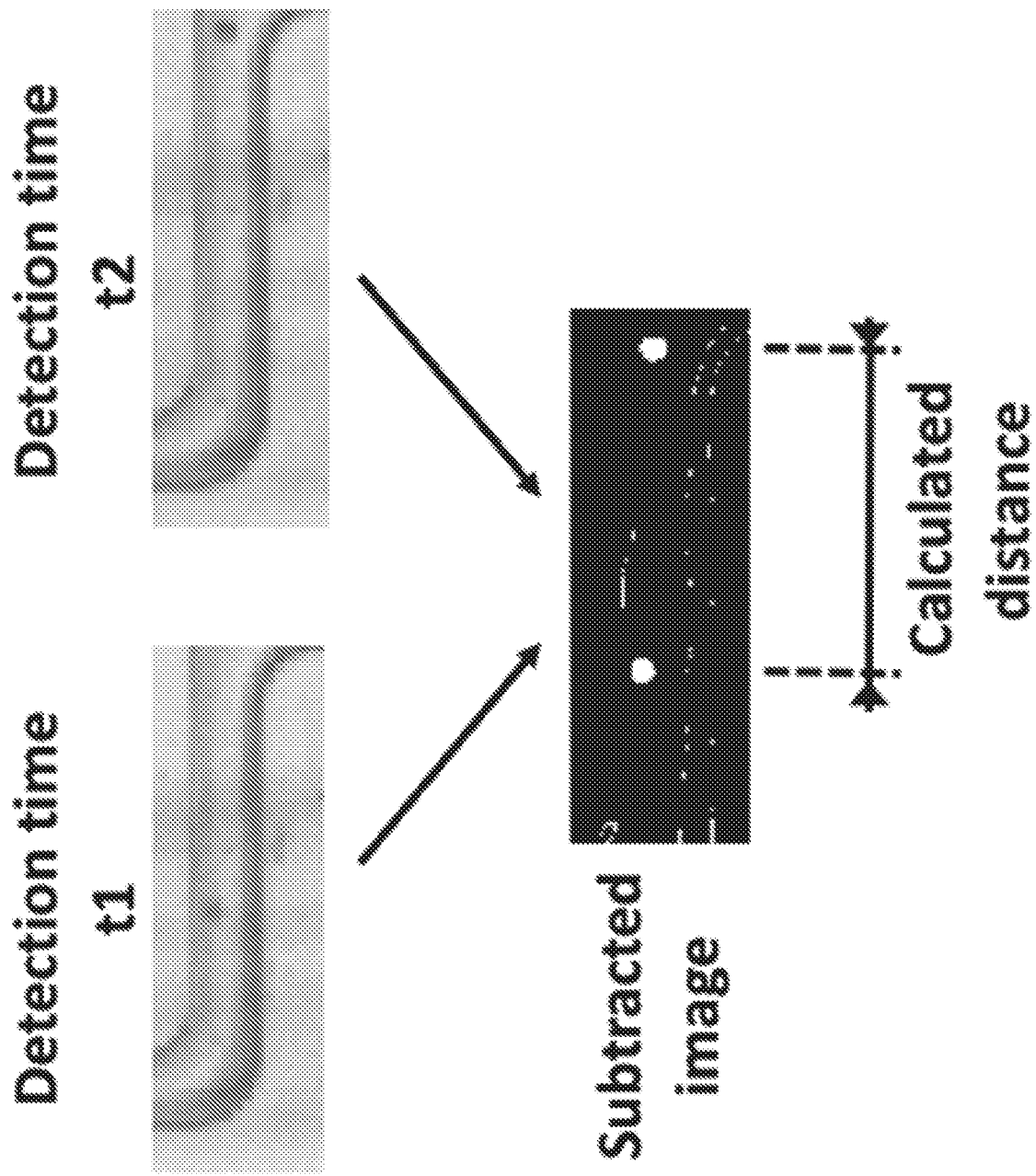
Figure 4:
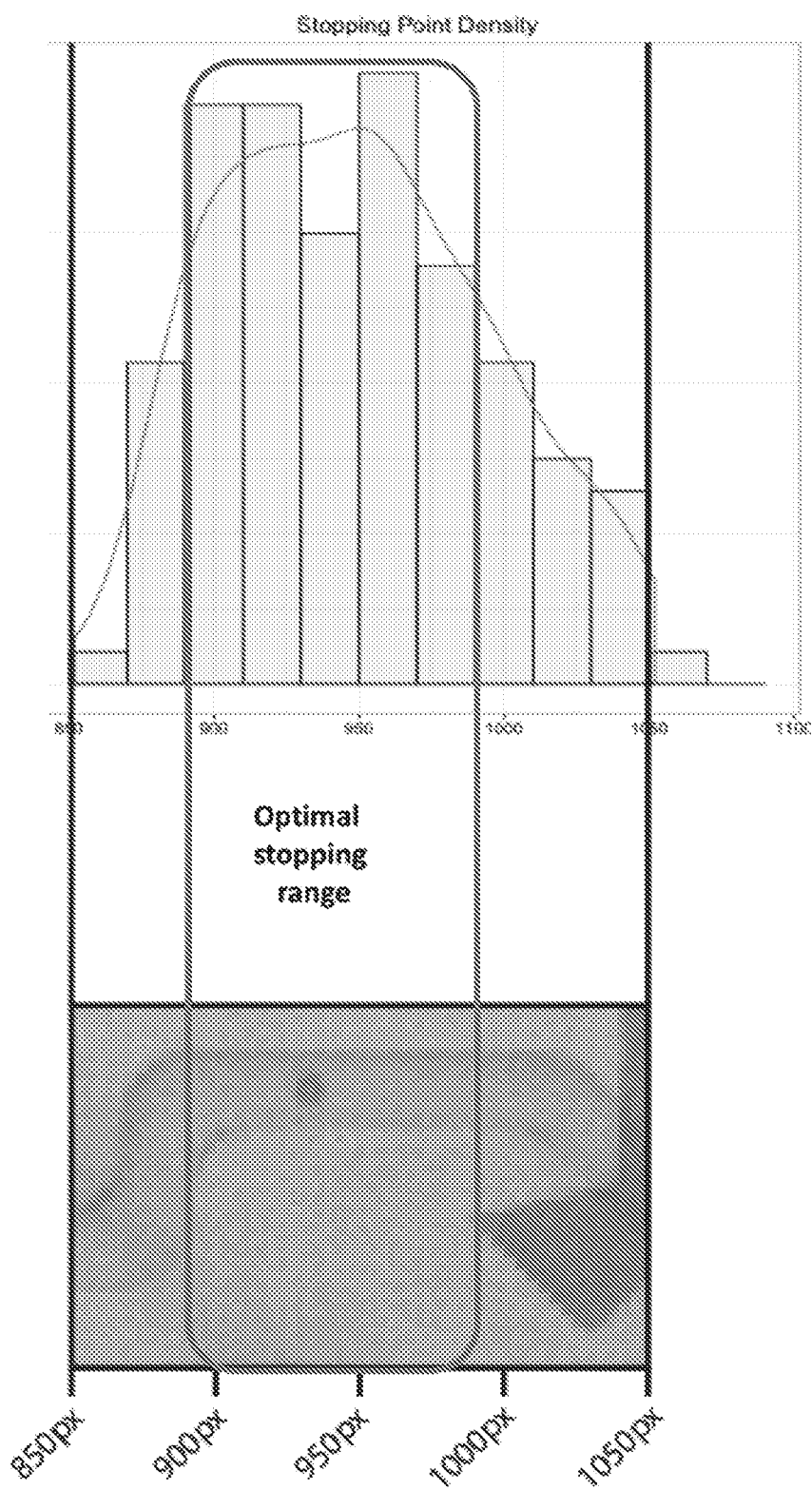
Figure 5:
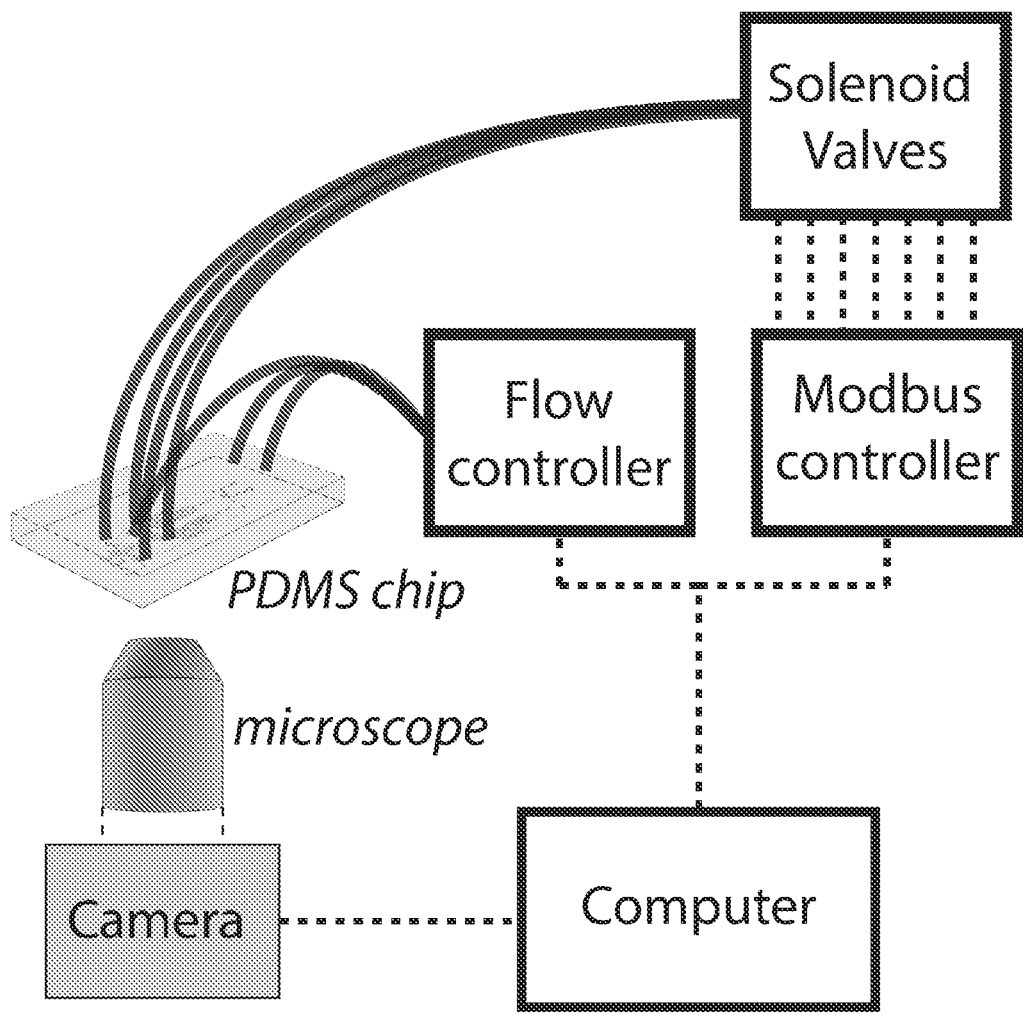
Figure 6:
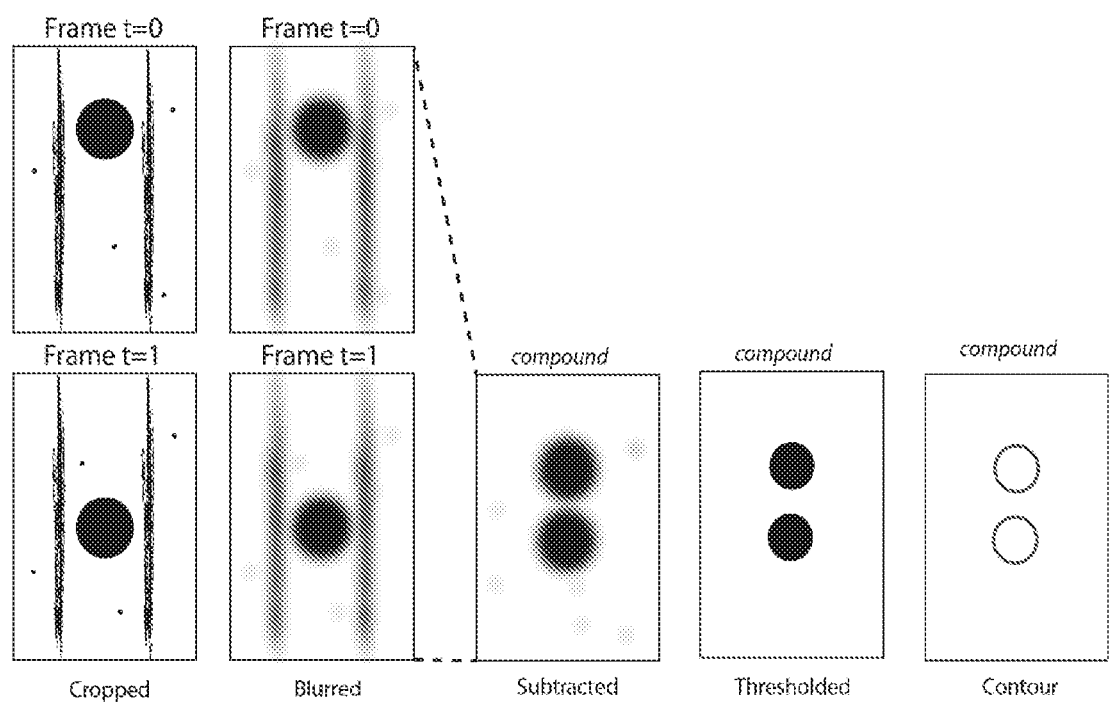
Figure 7:
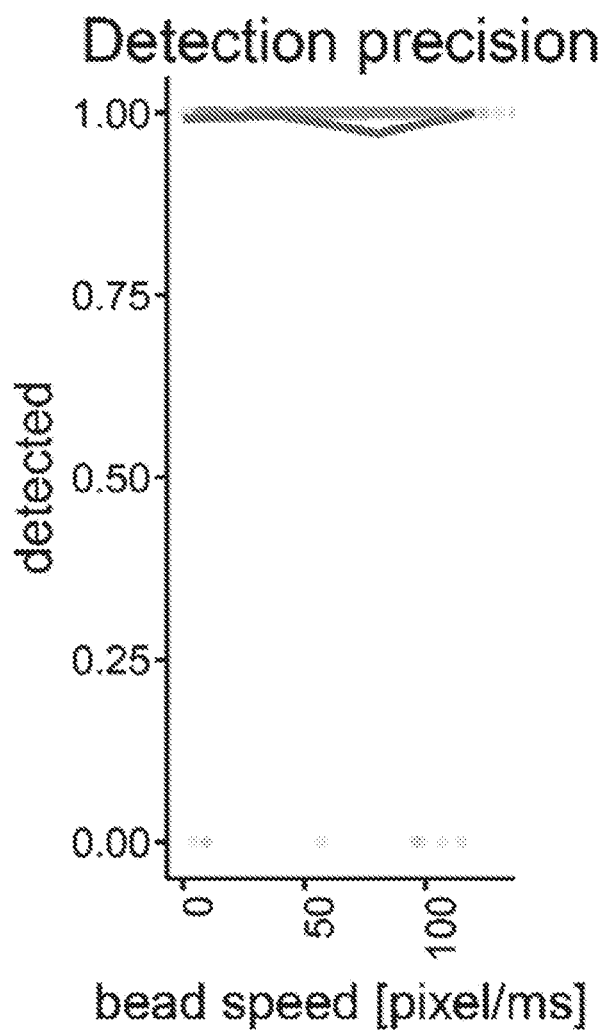
Figure 8:
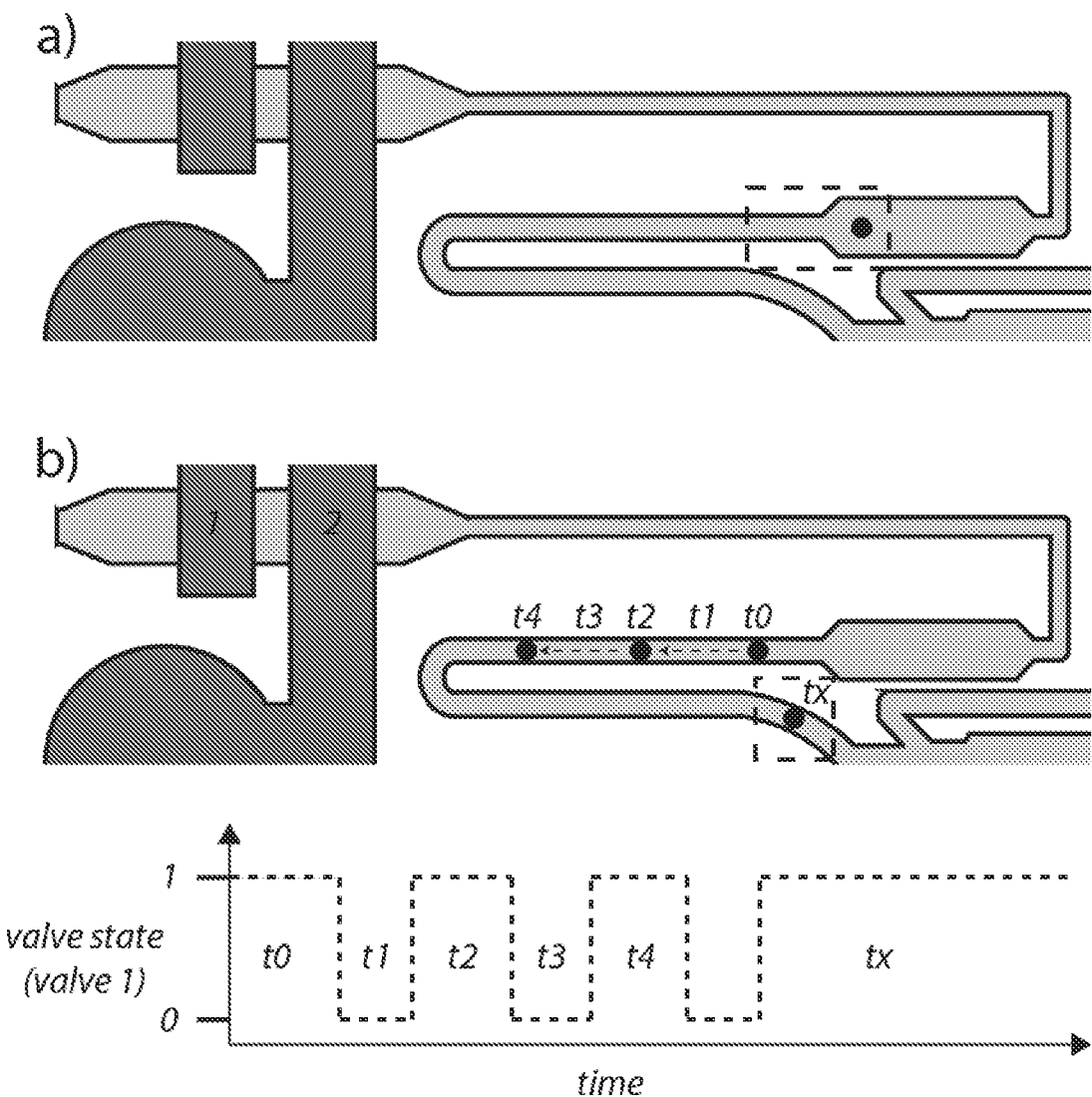
Figure 9:
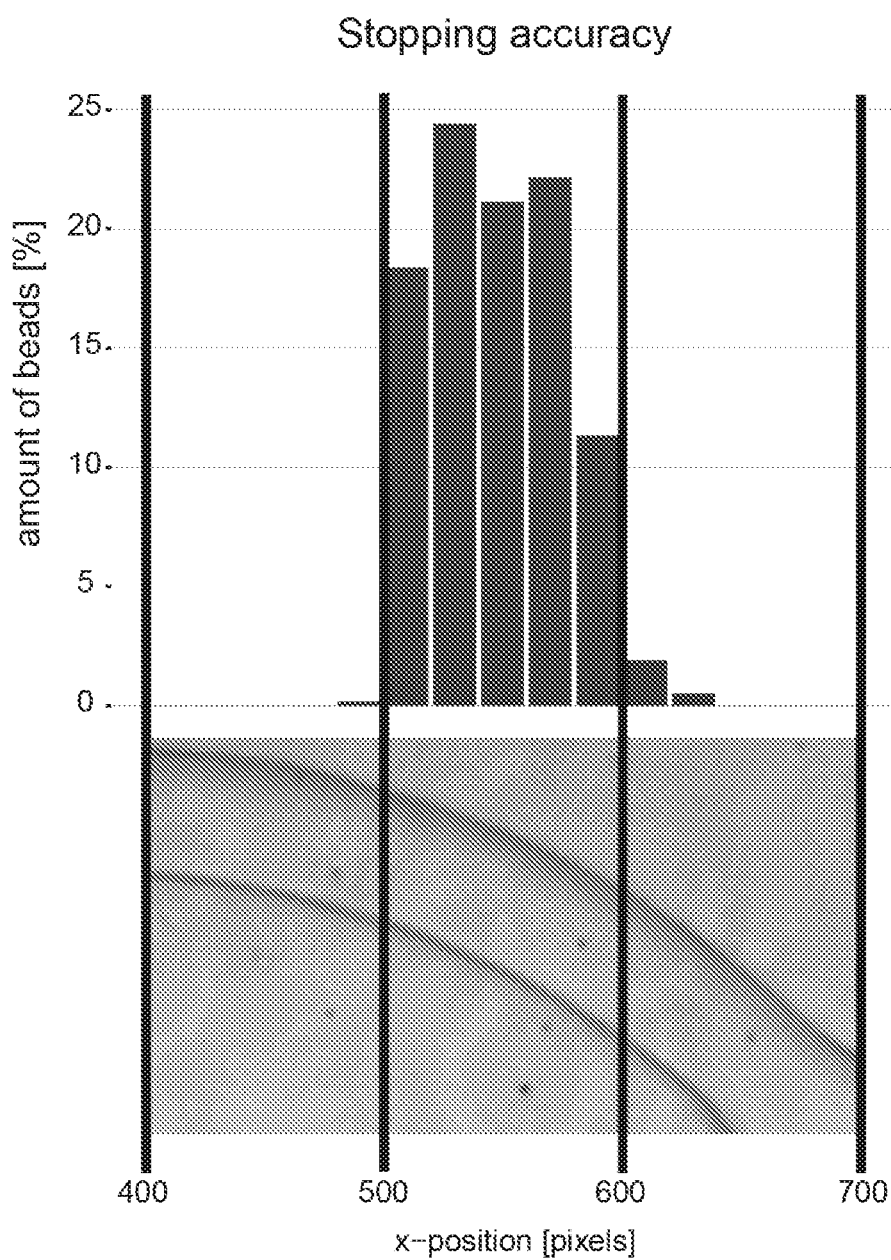
Figure 10:
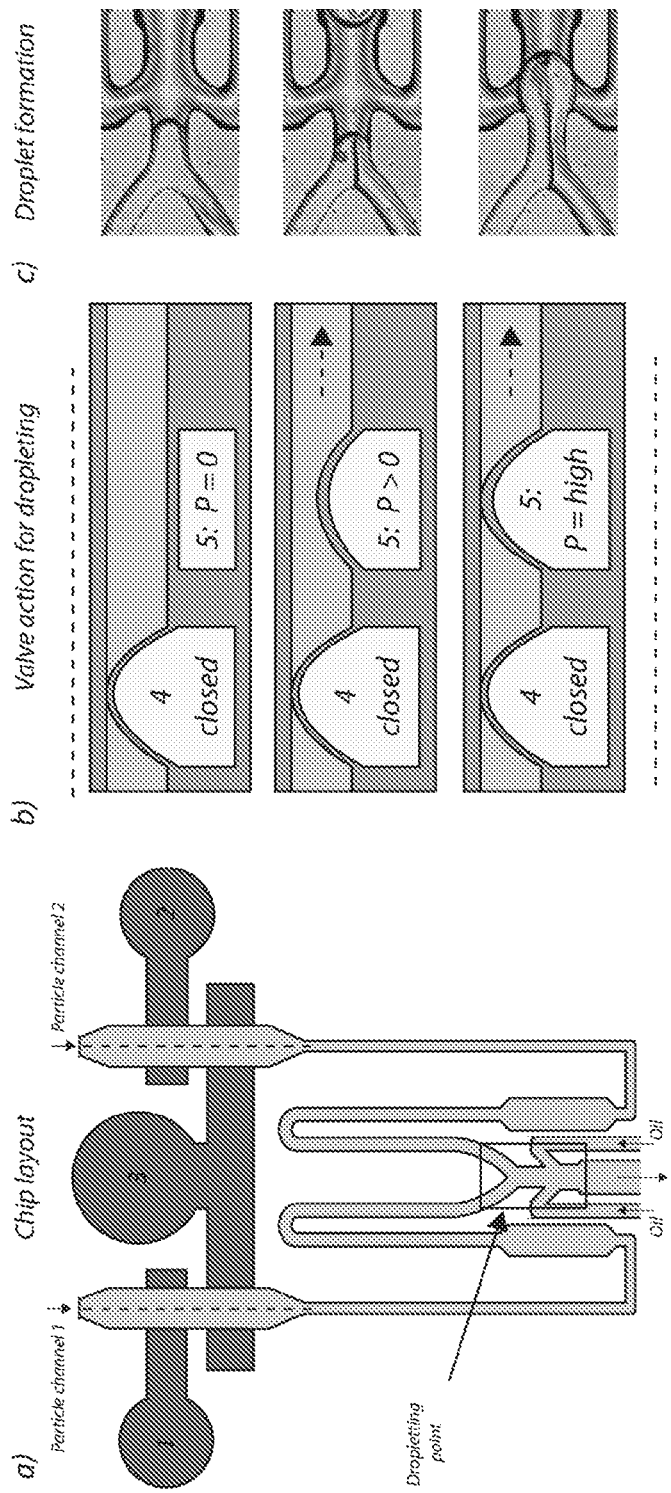
Figure 11:
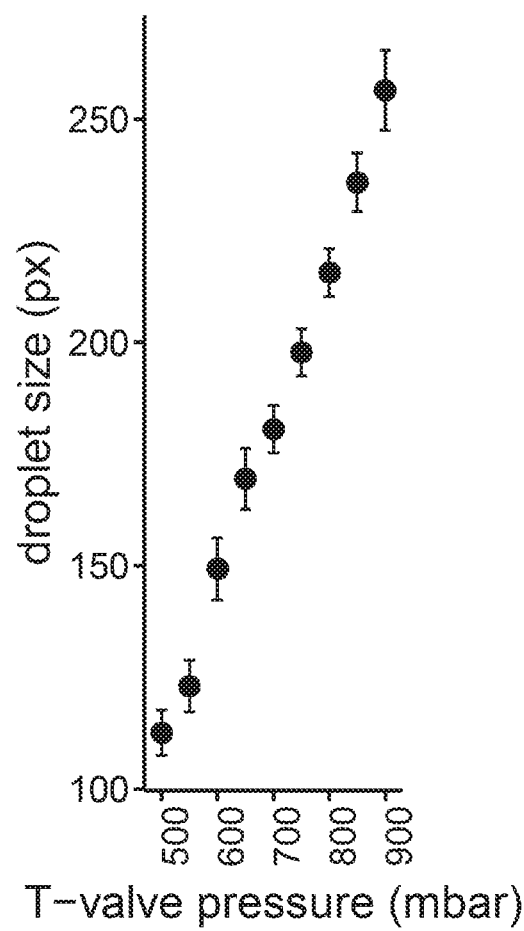
Figure 12:
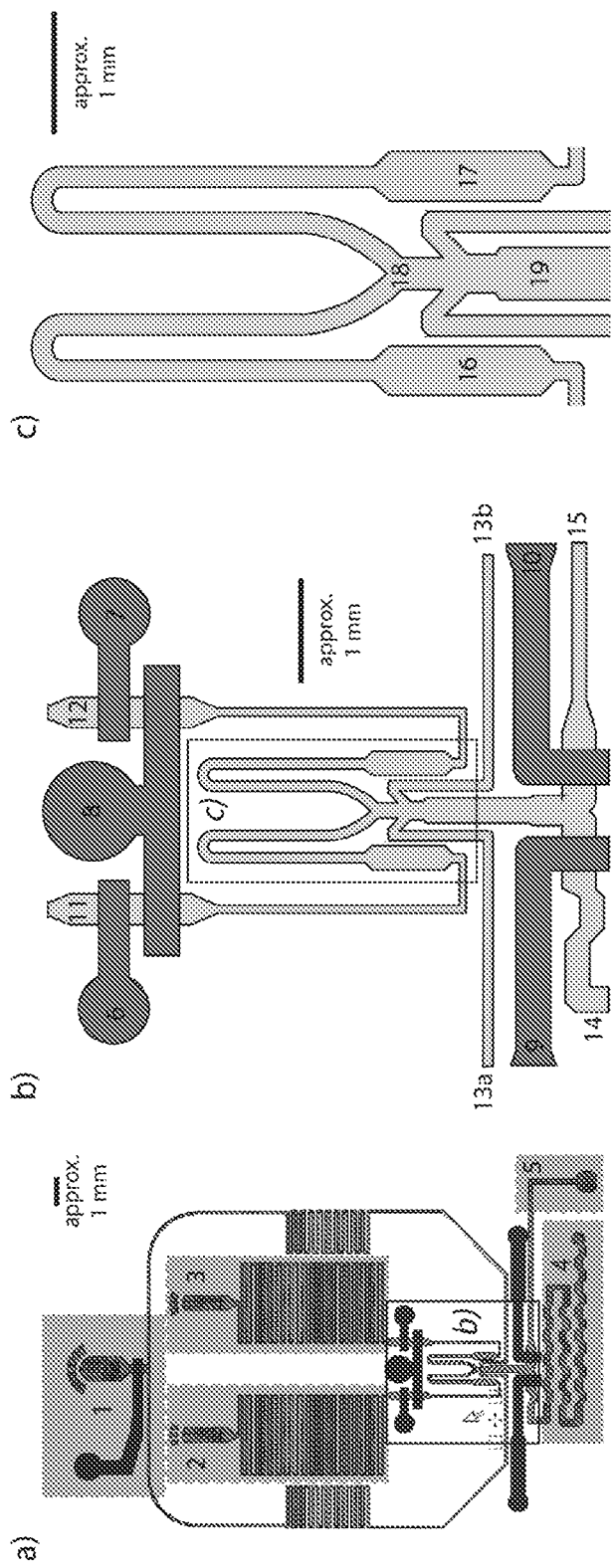
Figure 13:
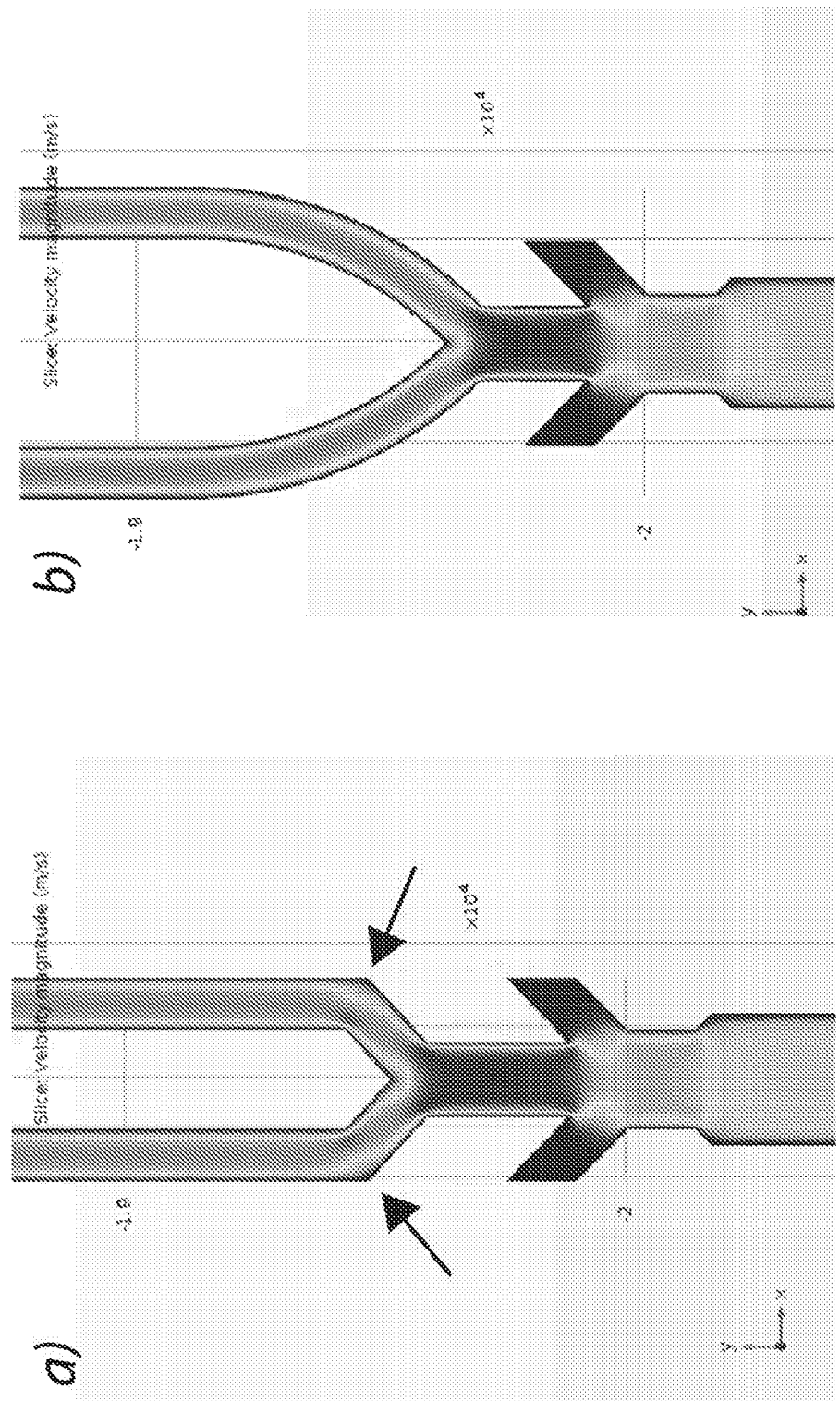
Figure 14:
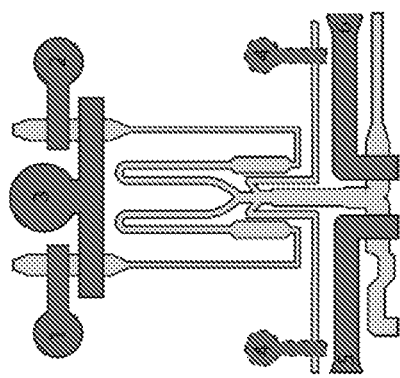
Figure 15:
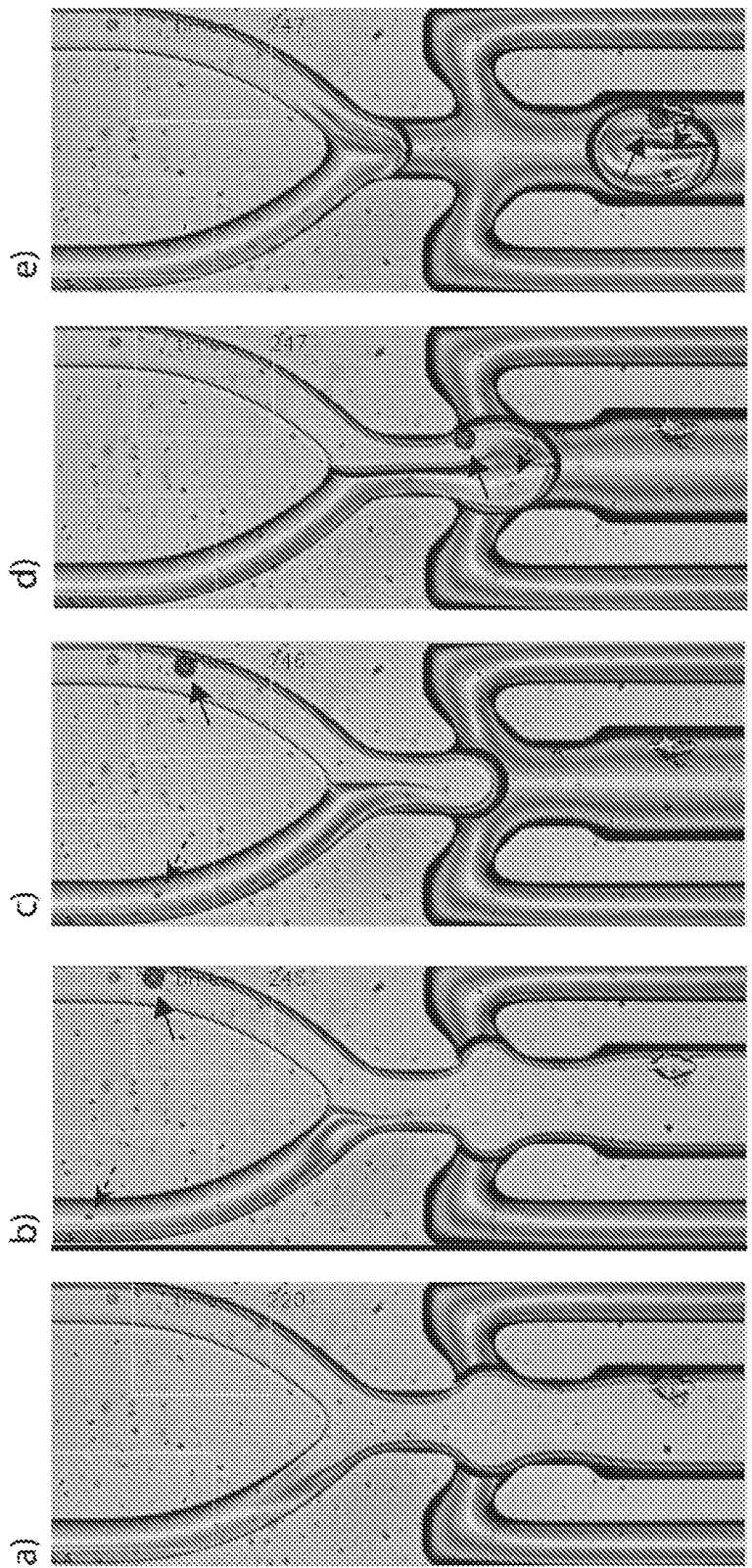
Figure 16:
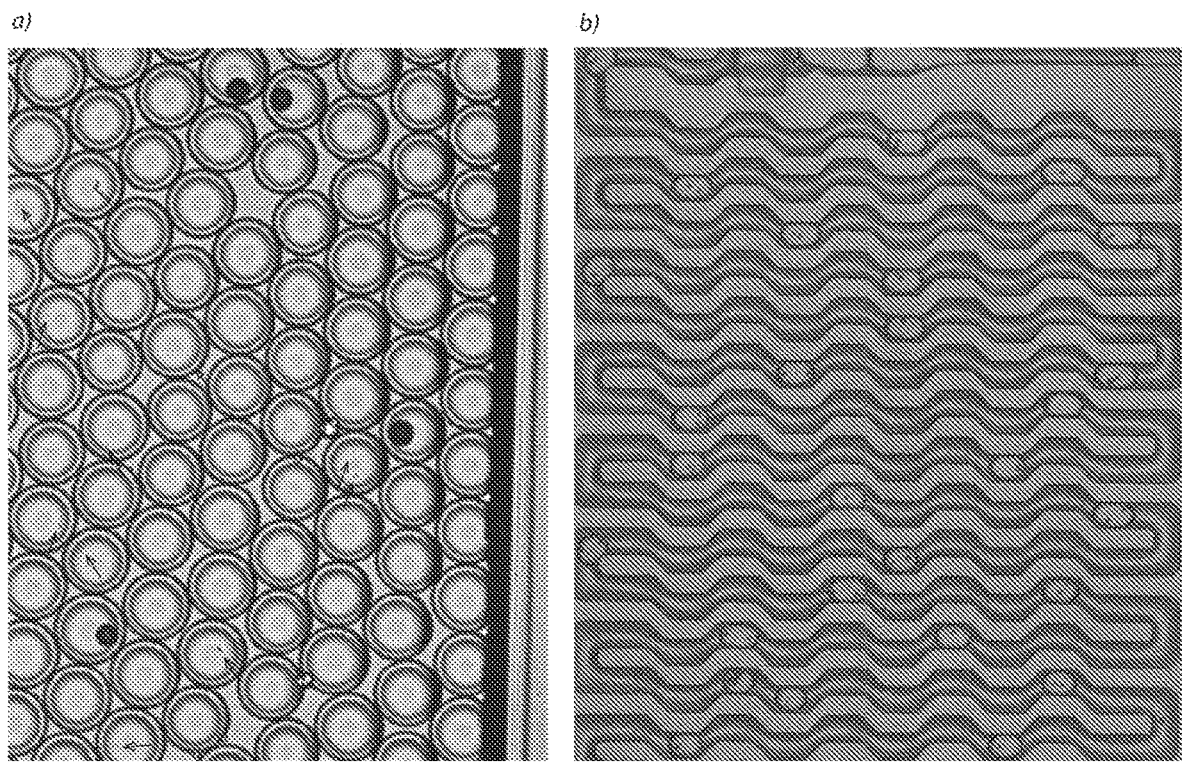
Figure 17:
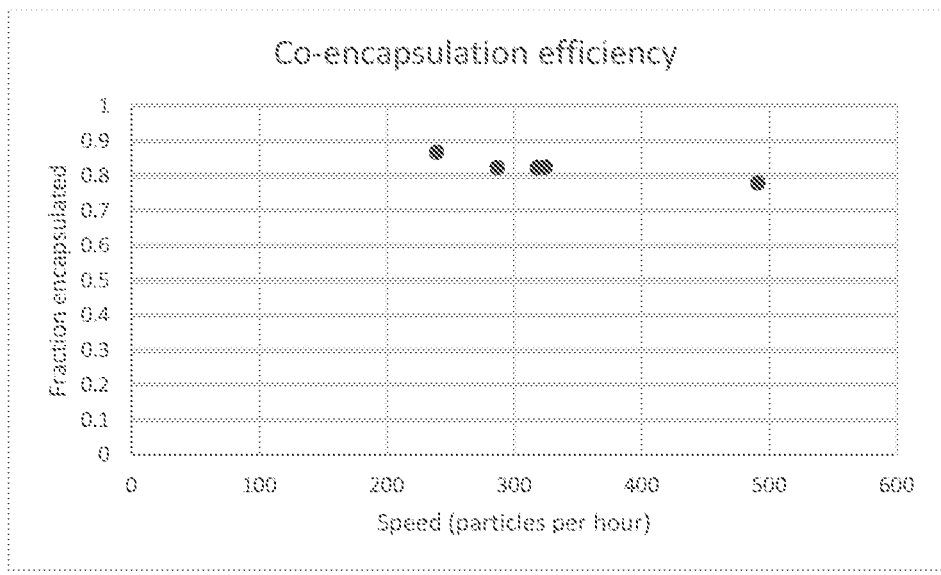

The above object, features and other advantages of the present invention will be best understood from the following detailed description in conjunction with the accompanying drawings, in which:

FIG. 1 shows an overview of a device or system of the present disclosure, where A shows a full microfluidic chip design; dark and light grey correspond to valves and microchannels respectively, B shows digital circuits elements for automation of microfluidic operations, C is a photograph of four microfluidic chips; a common USB drive is shown for size comparison;

FIG. 2 shows a sequence of event in the co-encapsulation area, where A shows a waiting phase of beads and cells, B shows Beads and cells precisely positioned by the software in the stop position, C shows Cells and beads ejected in the same droplet by actuation of the T-valve, FIG. 3 shows a speed measurement of moving particles, two subsequent images of a moving particle are subtracted from each other, resulting in two round shapes, the distance between the shapes, and time difference between frames can be employed to calculate particle speed;

FIG. 4 shows an experimentally derived position density distribution;

FIG. 5 shows information flow of the exemplary particle coordination system, a chip is monitored by a brightfield microscope connected to a high-speed camera, and images are analyzed computationally in real-time, once the software detects a particle moving on the chip, it sets valves states using a Modbus controller, and controls flow-rates using a flow-controller, the chip is connected for example with tubing to a solenoid valve setup and the flow controller;

FIG. 6 shows an image processing and particle detection approach, subsequent frames (we use for example frames that are taken 7 time points apart), are preprocessed by extracting regions of interest (ROIs), and blurred using a gauss filter, both images are subtracted from each other using absolute values, and thresholded for pixels with high intensity differences, on the thresholded images, contours are detected and analyzed;

FIG. 7 shows a performance test of particle detection, using the particle detection approach of the present disclosure, we are able to identify the vast majority of all particles (here microspheres of an average size of 40 um (microns)) flowing in the channels at a wide variety of speeds, each dot represents a single particle, the line the average detection fidelity;

FIG. 8 shows an oscillatory particle placement concept, flow channels are displayed in light grey, push-up valves are shown in dark grey, channel dimensions are described in FIG. 12, after detection of a particle in the detection region (a), the particle inlet valve (annotated as valve 1) is oscillated (b) to incrementally move particles towards a defined stopping region, while the valve is open the particle is able to move (tl) to the next position, until it is detected in the stopping region (tx);

FIG. 9 shows the stopping accuracy of oscillatory particle placement, using the oscillatory stopping mechanism particles can be placed in a small distinct region of a microfluidics channel, here the exemplary channel width is approximately 100 um (microns);

FIG. 10 shows the ejection of particles by dynamic valve pressurization, in a) a symmetric channel arrangement of 2 channels for dropleting is displayed, however the present disclosure also concerns single channel dropleting or multichannel dropleting, references 1 & 2 are valves for particle coordination in each channel, and 3 is the T-valve for liquid dispensing, channel width is described in FIG. 12, the dotted line represents the cross-section shown in b), after stopping of two particles the particle inlet valves (4, identical to a) 1 and 2) are closed, to eject equal amounts to form a microdroplet, the T-valve, here 5, (pressurizing both channels simultaneously) is dynamically pressurized by the flow controller, increasing pressures push liquid towards the dropleting area (Droplet formation), and form a drop, c) Shows the droplet formation at the dropleting point, as annotated in a);

FIG. 11 shows droplet size by dynamic valve pressurization, using the dynamic valve pressurization approach the volume of monodisperse droplets can by dynamically controlled by applying different pressures for liquid ejection;

FIG. 12 shows an exemplary chip layout of a deterministic particle processing system, here for deterministic co-encapsulation, a) shows a global view on the chip design, control layer is dark, flow layer is patterned where reference 1 is an oil inlet for droplet production, 2 Particle inlet 1 with resistor channels, 3 Particle inlet 2 with resistor channels, 4 Sample outlet for droplet collection with kinked mixing channels, 5 Waste outlet, an area of approximately 15 millimeter width and 20 millimeter height is shown b) shows a processing area of the chip, control layer is dark, flow-layer is light, 6 is a particle inlet valve 1 for stopping of particles, flow layer width in this area is 350 microns, control layer width is 300 microns, 7 is a particle inlet valve 2 for stopping of particles, 8 Ejection, or 'T-valve', 9 Sample outlet valve, 10 Waste outlet valve, 11 Particle inlet 1 channel, 12 Particle inlet 2 channel, 13 (a/b) oil channels, 14 Sample outlet channel, 15 Waste outlet channel, c) shows Particle coordination and a dropleting area of the chip, 16 Channel 1 widening for particle detection (250 microns channel width), 17 Channel 2 widening for particle detection (250 microns channel width), the widening of the channel leads to decreased flow velocities and hence slows particle down, 18 Dropleting point with optimized flow layout, 19 Dropleting channel, width of channel connecting 16/17 to 18 is 100 microns;

FIG. 13 shows flow optimization of a dropleting nozzle, dark color indicates slow velocity, light color indicates high velocity, dimensions are displayed in FIG. 12 a) Hydrodynamic simulation of a 90 degree dropleting area shows unequal flow speeds in the channel, leading to chip corners which can accumulate oil (arrows), as oil and water have different refractive indices, oil can disturb particle detection, b) Flow optimized nozzle design shows equal velocity across the two particle channels, preventing oil accumulation;

FIG. 14 shows valve states of co-encapsulation of particles, 0 means valve is open, 1 valve is closed, during particle detection both particle inlets and the T-valve are open, liquid is flowing in the waste outlet which is open as well, for stop particle, particle inlet 1 and 2 are closed, Flush oil opens the oil channel to remove waste buffers into the waste outlet, Eject particle pushes the particles in the dropleting channel by pressurizing the T-valve, Form & capture droplet is achieved by closing the waste channel, opening the sample channel, and opening the oil channel;

FIG. 15 shows the process of co-encapsulation, here of for example a cell and a bead, the system is detecting particles, dimensions are described in FIG. 12 (a) and stops particles once they are detected (b), after stopping waster liquid is flushed in the waste outlet (c) by opening the oil channel valve, next both particles are placed in a single droplet by ejecting fluid (d) from the channel and shearing the droplet by activation of the oil stream (e);

FIG. 16 is an output of the robot for deterministic co-encapsulation compared to a stochastic co-encapsulation system, a) shows the output of stochastic co-encapsulation of cells (arrows) and beads, showing no successful co-encapsulations in the field-of-view, b) shows that using the deterministic co-encapsulation system nearly perfect co-encapsulation output can be achieved, channel width is approximately 250 microns;

FIG. 17: Shows the co-encapsulation efficiency and speed achievable by deterministic co-encapsulation of particles from a single channel Here the fraction of the total number of particles observed in one channel which successfully was co-encapsulated with particles form the other channel is displayed.

Herein, identical reference numerals are used, where possible, to designate identical elements that are common to the Figures.

DETAILED DESCRIPTION OF SEVERAL EMBODIMENTS

The present invention concerns a device or microrobotic system comprising for example microfluidics, droplet microfluidics, and real-time image processing. A set of micromechanical valves for microparticle position with accuracy can be included. The system may be configured for the automation of image processing and on-chip microfluidic operation. The system may also be configured to implements a machine learning model for the automated calibration and operation of the device.

The present invention relates to the on-chip integration of multilayer microfluidics and droplet microfluidics. A system can be configured to carry out real-time image processing and/or machine learning. One object of the invention is to monitor and manipulate with accuracy the position of single microparticles (including single cells) in a microfluidic chip. This platform can for example deterministically co-encapsulate an arbitrary amount of single microparticles in an arbitrary amount of single water-in-oil droplets. The platform can for example be used to study lowly abundant cell populations with single-cell accuracy and with infinitesimal sample loss.

The microfluidic device or chip may include at least one inlet for introducing at least one object into the device and an oil inlet for introducing an oil that supports droplet formation into the device. The device may additionally include a co-encapsulation area or structure where the at least one object is encapsulated by the droplet, a microfluidic tubing or channel for transporting the at least one object to an entrance of the co-encapsulation area or structure.

The device may additionally include an oil supporting droplet formation microchannel connected to the microfluidic tubing or channel to place a liquid of the microfluidic tubing or channel in direct contact with the oil that supports droplet formation and a droplet microchannel or tubing for transporting the droplet.

The device or chip may include a single microfluidic tubing or channel for transporting the object, or two or multiple microfluidic tubings or channels.

Chip Fabrication

The microfluidic devices are fabricated by standard multilayer soft lithography techniques; more in detail, the device are conceived and designed by using the CAD software L-EDIT (Tanner, Mentor Graphics). Once designed the devices layout features are first imprinted on chromium masks and then transferred on 4-inches silicon wafers. For the wafers containing the features of the flow layer an exemplary 50 um-thick (or 60 microns thick) positive photoresist (AZ40XT, MicroChemicals GmbH) is used, while for the control layer, 50 um-thick negative photoresist (SU8 3050, Microchem) is used. After development, the flow layer wafer is reflown at 120 degrees Celsius for approximately 60 seconds to round the features. Once fabricated, the wafer molds are passivated by a 1% v/v water-based solution of trichloro(1H,1H,2H,2H-perfluorooctyl)silane (Sigma-Aldrich).

In order to fabricate the actual microfluidic device, two PDMS-based (SYLGARD® 184) solutions are used; for the control layer, a 20:1 w/w PDMS/curing agent solution is spun on the control layer mold in order to achieve a thickness of 80-100 um. For the flow layer, a 5:1 w/w PDMS/curing agent solution is poured directly onto the wafer in order to achieve a thickness of 0.4-0.6 cm. The two layers are partially cured at 80 degrees Celsius for 30 min, after which the flow layer is peeled off the wafer and aligned to the control layer. The two layer are left at 80 degrees Celsius for >1.5 hours in order to consolidate the bond. Subsequently the microfluidic devices are peeled off the second wafer and inlet holes are punched using a manual-punching machine (Syneo, USA). Finally, the so-obtained devices are bonded to a glass slide using oxygen plasma at 450 mTorr for 45 seconds exposure time. Before the experiment, in order to make the inner surface of the microfluidic channels hydrophobic and thus compatible with water-in-oil droplet formation, all the devices are treated with a 2% v/v water-based solution of trichloro(1H,1H,2H,2H-perfluorooctyl)silane.

Electronic Components Setup for Microfluidic Pressure Control

Once fabricated and treated with silane, the microfluidic devices are connected through the punched holes to water-filled microfluidic tubing (Tygon tubing). In order to control the pressure in the tubing in a fast and controllable way, we connected all tubings to solenoid valves (Festo). In turn, the solenoid valve actuation is controlled by a ETHERNET Programmable Fieldbus Controller (WAGO). The controller is connected through an Ethernet cable to a regular Windows desktop and it's programmed by our custom C++ software using the open source libmodbus library. For controlling particle speeds and precision pressure control a Fluigent FlowEZ flow controller is used, and controlled using C++ with the Fluigent SDK.

Real-Time Image Processing

On-chip real-time images were acquired through a Hot-Shot cc camera (nac Image Technology) mounted on a Nikon TS100 inverted microscope. Images were loaded and analyzed using OpenCV functions included in the same C++ software as above. For faster image acquisition (around 400 fps) a Ximea xiC MC031MG-SY camera was used.

On-Chip Droplet Formation and Microparticle Encapsulation

Droplets are formed by flow-focusing any water-based solution with fluorinated oil (Droplet Generation Oil, Bio-Rad). As the microparticle-containing water phase a 80% v/v PBS solution is used. In principle, any microparticle sufficiently big to be visible at the microscope and small enough to fit in the microfluidic channels (i.e. particles in the range 5-40 µm in diameter for example, or in the range 5-50 µm for example) can be used. In the calibration phase, either Hela-S3 cells or polystyrene particles of 18.0-24.9 µm in diameter (Spherotech) can be used.

Operation of the Microfluidic Chip.

In the first and simplest instance of the invention the microfluidic chip was designed in order for it to contain the minimum number of elements (channels, resistors, microvalves, etc.) required for deterministic co-encapsulation of two cells/microparticles in the same water-in-oil droplet.

The design is shown in FIG. 1A whereas the main sequence of events is depicted in FIG. 2. The experimental workflow is as follows:

1. The valves of the microfluidic chip (four of them are shown in FIG. 1C) are first connected to all the needed pressure sources, which are in turn regulated by a circuit composed of solenoid valves and a microcontroller (FIG. 1B).
2. Inlet 1 and 2 are loaded with microfluidic tubing containing cells or beads according to the specific experiment while the oil inlet is loaded with fluorinated oil that supports droplet formation.
3. The custom imaging software is started and a microscope camera is pointed at the co-encapsulation area.
4. The pressure in inlet 1 and 2 is raised in order to push the cell/bead suspension towards the co-encapsulation area (FIG. 2A). In the mean all the valves are open with the exception of the collection valve, which will open only for collection of co-encapsulated beads/cells.
5. When beads or cells reach the stop position, the imaging software triggers the closure of valve 1 or 2 depending on through which channel the beads/cells are arriving (FIG. 2B).
6. When both beads and cells are placed in the stop position, they can be optically inspected by the software, which can decide to proceed with co-encapsulation or flush out the unwanted cells/beads through the waste port.
7. If co-encapsulation is chosen, the waste valve is closed and the collection valve is opened.
8. Next, the T valve is actuated. The liquid displacement caused by the T valve actuation is identical in both bead and cell channels; as a consequence, the two microparticles approach the co-encapsulation point at the exact same time and are thereby encapsulated by the same droplet.
9. Points 1 to 7 are then repeated an arbitrary number of times until exhaustion of the biological sample.

Design of the Custom Imaging Software.

I. Particle Placement by Model Fitting

The custom imaging software was written in the programming language C++.

The essential image processing performed by the software is shown in FIG. 3. Images are recorded at ~25 frames per second. Each time a frame is recorded, it's compared by image subtraction to the previous frame. Once a bead it's detected, its position, travelling distance and speed are calculated. These variables are fed to a linear model which gives as an output the time of actuation of the valve responsible for bead/cell stopping.

The parameters of the model are updated in real-time during an experiment. The update rule is set to minimize the distance between the position where the bead/cell stops and the optimal stopping point position.

This process of image processing and model fitting is reiterated throughout an experiment. This is what allows the setup to acquire micrometer level accuracy in the microparticle positioning task and to become robust to unavoidable inter- and intra-experimental variations like manual system setup, differences in solution preparation etc.

As the name suggests, the fundamental property of DISCO is the ability of control bead/cell droplet co-encapsulation in a deterministic way. For this to happen beads and cells have to be positioned with micrometer accuracy. More precisely, beads/cells have to be placed in a position (or range), which ensures that during droplet formation they are encapsulated by the same droplet. In FIG. 4 this optimal range (which has been empirically determined) is depicted by the round-cornered rectangle. In the upper panel of FIG. 4 the experimental stopping position density distribution for beads is reported. As can be seen most of the beads are placed in the optimal position.

Deterministic Particle Placement and Encapsulation on Microfluidics Chips

The developed particle coordination system is a combination of machine vision and multilayer microfluidics to autonomous control movements and positions of particles on microfluidic chips. The system utilizes a brightfield microscope attached to a camera to stream images in real-time to a computer. The computer is analyzing the images and actuating flow control lines and solenoid valves, to control movements on chip. The overall information flow is summarized in FIG. 5.

I. Particle Detection by Machine Vision

To precisely place and move particles on a microfluidics chip, a machine-vision approach was employed to detect moving spheres on a microfluidics chip. The approach relies on identification of moving shapes between subsequent images by image subtraction, thresholding of the compound image, and contour detection on the resulting binary image. A visual representation of the particle detection approach is depicted in FIG. 6.

In detail, the steps of detections are the following:
1. An input microscopy image is reduced (by cropping) to regions of interests (ROIs).
2. Cropped images are blurred by a Gaussian filter to remove single pixel artifacts.
3. Subsequent images from the same ROI are subtracted from each other to an absolute value. Of note, we also considering images subsequent that have multiple images in-between one another, currently we use a buffer of 7 images.
4. After the subtraction, the compound image is thresholded to a binary image. Thresholds employed in this step depend on the opacity of the particle to be detected.
5. Contour detection is applied to the binary image.
6. Finally, contours are pre-evaluated by their pixel area, and contours reaching a defined threshold are further analyzed for their circularity by calculating the ratio of perimeter to area. This strategy is tailored to detection of round particles in brightfield microscopy and can be easily adapted to alternative scenarios.

This simplistic approach for particle recognition on microfluidic chips is coded in C++ and the OpenCV computer vision library. The current multithreaded implementation of this code is able to real-time process 400 frames per second, and each frame is processed within a few milliseconds causing very little delay. The performance and reliability was tested on 40 um microspheres flowing in microfluidic channels and the code showed robust performance over a wide range of particle speeds, detecting over 98% of all particles flowing in the channel, as shown in FIG. 7.

II. Particle Placement by Valve Oscillation

Particles movements are coordinated by firstly detecting them using the previously described machine vision approach, and subsequent microfluidic valve closure. As peristaltic microfluidic valves are displacing liquids inside a microfluidics channel, precise placement by mere valve closure is impractical. For this reason, in this approach, we detect moving particles in a dedicated detection region on the chip, displayed in FIG. 8, a, and place them by oscillatory valve actuation. For this we continuously open and close the inlet valve to move the particle incremental distances in the channel, as shown in FIG. 8, b. The particle is moved towards the desired stop point, or stopping region, which is simultaneously to valve oscillation monitored by the particle detection software. Once the particle is detected in the stopping region valve oscillation is stopped. We evaluated the placement precision of this particle stopping approach by placing 40 um microspheres, which was possible with excellent precision, observable in FIG. 9.

III. Droplet On-Demand Production

For processing of particles, or assembly of spatially segregated compartments, particles are placed inside water-in-oil microdroplets. The channel arrangement for producing droplets contains the sample holding channel, and an additional channel joining the sample channel containing fluorinated oil. As after particle stopping the aqueous phase is not moving, an additional valve, the 'T-valve' was placed behind the particle stopping valve to displace liquid in the sample channel. Channel arrangements are shown in FIG. 10, a. When a particle is stopped and the oil flow is deactivated, closing of the T-valve ejects liquid, the mechanism is depicted in FIG. 10b, including the particle, beyond the oil channel, as displayed in FIG. 10c. Hence, once the oil channel is opened, the liquid phase is getting sheared by the oil phase and a droplet is formed. Furthermore, the size of the droplet can be regulated by applying different pressures on the T-valve, dispensing different amounts of liquid.

To demonstrate the flexible formation of monodisperse droplets from stopped flows, a flow-controller was connected to the T-valve, and varying pressures applied to the sample channel. It was possible to produce droplets of a wide range of sizes in a highly reproducible manner, shown in FIG. 11.

Deterministic Co-Encapsulation Chip

Using the particle coordination and encapsulation workflow a DeterminIStic CO-encaspulation robot was developed. The overall chip layout, shown in FIG. 12a, comprises of an oil inlet controllable by a valve (1), two separate particle inlets (2, 3), a sample outlet (4), and a waste outlet (5). The co-encapsulation area, as depicted in FIG. 12b, contains the previously described control area for two particles. Downstream of the dropleting point (annotated in FIG. 10, c) two valves (9, 10) for droplet sorting were integrated. This arrangement allows for active separation of e.g. excess buffers into the waste port (15) from particle containing droplets into the sample port (14). The dropleting point shown in FIG. 12c shows both detection regions (16, 17), the dropleting point (18), and the dropleting channel (19). In order to prevent oil accumulations in the sample channels which can arise through unequal flow velocity in the channels, hence dead spaces, the dropleting nozzle was flow optimized as shown in FIG. 13.

For setting up a microfluidic chip solenoid valve lines are connected to all valves (FIG. 12, b: 6, 7, 9, 10) and primed with water. The T-valve, as it is dynamically pressured, is connected to the flow controller and primed with water. Particle solutions are introduced in channel inlets (FIG. 12, a: 2, 3) and connected to the flow controller, and fluorinated oil in the oil channel (FIG. 12, a: 1) and connected to a continuous pressure line (1.7 psi). The sample outlet (FIG. 12, a: 4) is connected to a collection vessel, and the waste outlet (FIG. 12, a: 5) is connected to a waste vessel. All connections are established with rubber tubing. The microscope, and the connected camera, is pointed at the co-encapsulation, with a field-of-view approximately the layout of FIG. 12c.

The processing workflow is described below. FIG. 14 shows a valve state chart for different steps of particle processing, FIG. 15 microscopic images of the co-encapsulation process.
1. The pressure in inlet 1 and 2 is raised by the flow controller in order to push the cell/bead suspension towards the co-encapsulation area. The valves are set to the 'detect particle' state (FIG. 14).

2. When beads or cells reach the detection region of interest, the imaging software triggers the closure of valve 1 or 2 depending the channel the beads/cells are detected.
3. Subsequently oscillatory particle placement is executed (as described in FIG. 8) to position the particle in the correct stopping position.
4. When both particles are placed in the stop position, the 'stop particle' state is reached (FIG. 14). Optionally particles can be inspected by computer vision inside the software, unwanted particles be discarded through the waste port and new particles captured for processing.
5. If the particles are chosen to be co-encapsulation, buffer residues are flushed out of the system by opening the oil-valve for a short period of time, before the waste valve is closed and the collection valve is opened. Valve configuration for flushing is termed 'flush oil' (FIG. 14).
6. Next, the T valve is pressurized by applying defined pressures, leading to the ejection of the co-encapsulation droplet, termed 'eject particle' state (FIG. 14). The symmetric arrangement of the T-valve on both sample channels leads to simultaneous liquid dispension of both channels, hence both particles approach the co-encapsulation point at the exact same time and are encapsulated by the same droplet.
7. Finally, the droplet is sheared and captured in the sample channel by opening the oil channel, and switching from the waste to the droplet channel Valve states are described in 'form & capture droplet' in FIG. 14.
8. The process is continued by switching back to the 'detect particle' state, and is continued until enough particles are processed, or until the sample is exhausted.

The improvement form stochastic co-encapsulation, shown in FIG. 16a, to deterministic co-encapsulation relying on or robotic approach is depicted in FIG. 16b, in which nearly no faulty encapsulation events are visible. Moreover, the deterministic approach has proven to be vastly more efficient in co-encapsulation particles in microdroplets (compared to approximately 5-10% in stochastic co-encapsulation), as depicted in FIG. 17. Noteworthy, the approach was verified to work with cells as well, as shown in FIG. 15.

A novel approach for particle coordination is disclosed by combining machine vision and multilayer microfluidics into a particle processing robot. The approach relies on a simplistic particle detection approach, here demonstrated to be compatible with cells and microbeads, yet generally applicable to particles detectable by microscopy. The approach, besides being highly reliable in detecting particles, is due to its simplicity also compatible with high-speed imaging. Here a parallelized version of the code is used at 400 frames per second in real-time. In combination with oscillatory valve actuation, it enables highly precise particle movement and placement on microfluidic chips. In contrast to currently employed methods for particle processing, our method uniquely allows for particle stopping without traps, and automated controlled particle movement on chip. Employing a new droplet on demand approach using dynamic pressurization of a peristaltic microfluidic valve, the particle manipulation system shows to be compatible with microdroplets.

In a first application, a DetermnInISctic CO-encapsulation (DISCO) system was developed, based on the process and design schemes for particle manipulation. Specifically, two particles (microbeads and cells are shown) are detected, stopped at a defined position, and encapsulated in a droplet. Using the particle coordination approach it was possible to develop an autonomous robot to undertake this task which vastly improves co-encapsulation (75-90%) efficiencies of particles, and has a close to perfect co-encapsulation success rate. As cutting edge single-cell processing methods, for e.g. RNA sequencing (Macosko et al. 2015), rely on co-encapsulation of RNA capturing particles with cells, the uniquely high efficiency and reliability of DISCO will allow for processing for rare-samples, e.g. circulating tumor cells.

BIBLIOGRAPHY

Macosko, E. Z., Basu, A., Satija, R., Nemesh, J., Shekhar, K., Goldman, M., et al. (2015). Highly Parallel Genome-wide Expression Profiling of Individual Cells Using Nanoliter Droplets. *Cell*, 161(5), 1202-1214. doi:10.1016/j.cell.2015.05.002

Dura, B., Dougan, S. K., Barisa, M., Hoehl, M. M., Lo, C. T., Ploegh, H. L., & Voldman, J. (2015). Profiling lymphocyte interactions at the single-cell level by microfluidic cell pairing. *Nature Communications*, 6, 5940. doi: 10.1038/ncomms6940

The invention claimed is:
1. A microfluidic device or chip including:
a first inlet for introducing a first object into the device and a second inlet for introducing a second object into the device;
an oil inlet for introducing an oil that supports droplet formation into the device or a droplet forming substance inlet for introducing a droplet forming substance into the device;
a co-encapsulation area or structure where the first and second objects are encapsulated by the droplet, the co-encapsulation area or structure being in fluid communication with the oil inlet or the droplet forming substance inlet;
a first microfluidic tubing or channel in fluid communication with the first inlet and with the co-encapsulation area or structure, the first microfluidic tubing or channel being configured to receive the first object from the first inlet and to transport the first object to an entrance of the co-encapsulation area or structure; and a second microfluidic tubing or channel in fluid communication with the second inlet and with the co-encapsulation area or structure, the first microfluidic tubing or channel being configured to receive the second object from the second inlet and to transport the second object to the entrance of the co-encapsulation area or structure;
an oil supporting droplet formation microchannel or droplet forming substance microchannel in fluid communication with the oil inlet or the droplet forming substance inlet, and connected to both the first microfluidic tubing or channel and to the second microfluidic tubing or channel to place a liquid of the first and second microfluidic tubings or channels in direct contact with the oil that supports droplet formation or the droplet forming substance; the oil supporting droplet formation microchannel or the droplet forming substance microchannel including the co-encapsulation area or structure;
a droplet microchannel or tubing for transporting the droplet for collection, the droplet microchannel or tubing being in fluid communication with the oil supporting droplet formation microchannel or droplet forming substance microchannel;

wherein the microfluidic device or chip further includes:
> a first object stopping valve connected to the first microfluidic tubing or channel and located upstream of the co-encapsulation area or structure, the first object stopping valve being configured to stop the first object and position the first object in a stop position or stop region located upstream of the co-encapsulation area or structure; and a second object stopping valve connected to the second microfluidic tubing or channel and located upstream of the co-encapsulation area or structure, the second object stopping valve being configured to stop the second object and position the second object in a stop position or stop region located upstream of the co-encapsulation area or structure; and
>
> an ejection valve connected to both the first microfluidic tubing or channel and the second microfluidic tubing or channel, the ejection valve being configured to simultaneous dispense liquid of the first microfluidic tubing or channel and liquid of the second microfluidic tubing or channel to displace both the first and second objects simultaneously to the co-encapsulation area or structure for encapsulation of both the first and second objects inside the same droplet.

2. The microfluidic device or chip according to claim 1, wherein the first and second microfluidic tubings or channels are configured to transport a liquid in first and second microfluidic tubings or channels at the same velocity.

3. A system including the microfluidic device or chip according to claim 1.

4. The system according to claim 3, further including a camera configured to image the at least one object.

5. The system according to claim 3, further including a processor configured to operate a camera and capture images.

6. The system according to claim 5, wherein the processor is further configured to detect movement of the first or second object.

7. The system according to claim 5, wherein the processor is configured to determine from the images when each of the first and second objects reaches their respective stop positions or regions, and further configured to trigger a closure of the first and second object stopping valves when it is determined from the images that each of the first and second objects reaches their respective stop positions or regions.

8. The system according to claim 7, wherein the processor is configured to optically inspect the first and second objects in the stop positions or regions, and to proceed with co-encapsulation of the first and second objects.

9. The system according to claim 8, wherein the processor is configured to close a waste valve and open a collection valve.

10. The microfluidic device or chip according to claim 1, wherein the ejection valve is configured to displace, when actuated, liquid in the first and second microfluidic tubing or channels and simultaneously displace the first and second objects to a co-encapsulation point at the exact same time to thereby encapsulate the first and second object in the same droplet.

11. The microfluidic device or chip according to claim 10, wherein the microfluidic device or chip includes a processor configured to actuate the ejection valve.

12. The microfluidic device according to claim 11, wherein the ejection valve is a T-valve.

13. The system according to claim 9, wherein the system is configured to actuate the first stopping valve and the second stopping valve in an oscillatory manner to displace the first or second object an incremental distance.

14. The system according to claim 13, further including pressure sources connected to the first and second object stopping valves.

15. The system according to claim 3, wherein the at least one object is a particle.

16. A method for operating a system according to claim 4 for forming a droplet comprising at least one object, the method including the steps of:
> introducing a first and second object into the device through a first and second inlet;
> introducing a droplet forming substance into the device through the droplet forming substance inlet;
> transporting the first object through first microfluidic tubing or channel and the second object through second microfluidic tubing or channel;
> stopping a first object inside the first and microfluidic tubing or channel upstream of the co-encapsulation area or structure using a first object stopping valve connected to the first microfluidic tubing or channel and located upstream of the co-encapsulation area or structure; and stopping a second object upstream of the co-encapsulation area or structure using a second object stopping valve connected to the second microfluidic tubing or channel and located upstream of the co-encapsulation area or structure;
> simultaneously displacing both the first object in the first microfluidic tubing or channel and the second object in the second microfluidic tubing or channel to the co-encapsulation point at the same time to encapsulate the first and second object in the same droplet using an ejection valve connected to both the first microfluidic tubing or channel and the second microfluidic tubing or channel, the ejection valve being configured to simultaneous dispense liquid of both the first microfluidic tubing or channel and the second microfluidic tubing or channel to permit the first and second objects to simultaneously move to the co-encapsulation point for encapsulation by the same droplet.

17. A droplet containing the first and second objects produced according to the method of claim 16.

18. The system according to claim 3, wherein the system is configured to carry out oscillatory actuation of the first and second object stopping valves to open and close the first and second object stopping valves to move the first and/or second objects towards their respective stop positions or stop regions.

19. The method according to claim 16, wherein oscillatory actuation of the first and second object stopping valves is carried out to open and close the first and second object stopping valves to move the first and second objects towards their respective stop positions or stop regions;
> the ejection valve is actioned to simultaneous dispense liquid of the first microfluidic tubing or channel and liquid of the second microfluidic tubing or channel to simultaneously displace the first and second objects to the co-encapsulation area or structure, and
> encapsulating the first and second objects inside the same droplet by flowing the droplet forming substance through the droplet forming substance inlet and in the droplet microchannel or tubing to shear the droplet.

* * * * *